United States Patent
Hart et al.

(10) Patent No.: US 6,699,232 B2
(45) Date of Patent: Mar. 2, 2004

(54) FLUID INJECTION APPARATUS WITH IMPROVED CONTRAST VISUALIZATION

(75) Inventors: Colin P. Hart, Queensbury, NY (US); Valerie M. Castora, Fort Ann, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/797,473

(22) Filed: Mar. 1, 2001

(65) Prior Publication Data

US 2002/0123737 A1 Sep. 5, 2002

(51) Int. Cl.[7] .............................................. A61M 25/00
(52) U.S. Cl. ..................... 604/523; 604/69.01; 604/264; 604/528; 604/533; 604/915
(58) Field of Search ............................ 604/69.01, 97.01, 604/99.01, 101.02, 101.04, 113, 264, 523, 533, 528, 915; 606/194

(56) References Cited

U.S. PATENT DOCUMENTS

| | | |
|---|---|---|
| 3,674,009 A | 7/1972 | Williamson |
| 3,701,345 A | 10/1972 | Heilman et al. |
| 4,006,736 A | 2/1977 | Kranys et al. |
| 4,024,864 A | 5/1977 | Davies et al. |
| 4,250,887 A | 2/1981 | Dardik et al. |
| 4,370,982 A | 2/1983 | Reilly |
| 4,502,488 A | 3/1985 | Degironimo et al. |
| 4,533,346 A | 8/1985 | Cosgrove, Jr. et al. |
| 4,551,133 A | 11/1985 | Zegers de Beyl et al. |
| 4,634,431 A | 1/1987 | Whitney et al. |
| 4,695,271 A | 9/1987 | Goethel |
| 4,767,406 A | 8/1988 | Wadham et al. |
| 4,812,724 A | 3/1989 | Langer et al. |
| 4,854,324 A | 8/1989 | Hirschman et al. |
| 4,861,340 A | 8/1989 | Smith et al. |
| 4,877,956 A | 10/1989 | Priest |
| 4,919,650 A | 4/1990 | Feingold et al. |
| 4,952,205 A | 8/1990 | Mauerer et al. |
| 5,014,715 A | 5/1991 | Chapolini |
| 5,114,423 A * | 5/1992 | Kasprzyk et al. ............. 606/27 |
| 5,137,514 A | 8/1992 | Ryan |
| 5,139,484 A | 8/1992 | Hazon et al. |
| 5,236,416 A | 8/1993 | McDaniel et al. |
| 5,322,511 A | 6/1994 | Armbruster et al. |

(List continued on next page.)

FOREIGN PATENT DOCUMENTS

| | | |
|---|---|---|
| EP | 0 702 966 A2 | 3/1996 |
| EP | 0 346 950 B2 | 9/1997 |
| WO | WO 99/24094 | 5/1999 |
| WO | WO 00/59569 | 10/2000 |

*Primary Examiner*—Robin O. Evans
(74) *Attorney, Agent, or Firm*—Marshall, Gerstein & Borun LLP

(57) ABSTRACT

An apparatus and method for manually injecting fluid into a patient with improved contrast visualization are disclosed. The apparatus includes a syringe having a cylinder in which a plunger is reciprocatingly mounted. The syringe is connected to a manifold which itself is connected to a source of radiopaque contrast. Retraction of the plunger within the cylinder draws contrast into the cylinder, and depression of the plunger forces the contrast through the manifold and into a patient through a catheter. In order to increase the speed of injection and thus the visualization of the contrast, an improved visualization device is provided which may be provided in the form of a heater or, alternatively, in the form of an expandable catheter. The heater may be positioned anywhere within the apparatus to elevate the temperature of the contrast material, which in turn reduces its viscosity and thereby increases the speed with which fluid may be injected. The expandable catheter, may be used to restrict blood flow through a vascular structure so that the contrast material may be injected into the patient with lessened resistance and dilution from blood flow.

10 Claims, 3 Drawing Sheets

U.S. PATENT DOCUMENTS

| | | | |
|---|---|---|---|
| 5,417,689 A | * | 5/1995 | Fine .......................... 606/41 |
| 5,451,208 A | * | 9/1995 | Goldrath ..................... 604/515 |
| 5,485,831 A | | 1/1996 | Holdsworth et al. |
| 5,496,311 A | * | 3/1996 | Abele et al. .................. 606/28 |
| 5,515,851 A | | 5/1996 | Goldstein |
| 5,562,614 A | | 10/1996 | O'Donnell |
| 5,569,208 A | | 10/1996 | Woelpper et al. |
| 5,573,515 A | | 11/1996 | Wilson et al. |
| 5,611,340 A | | 3/1997 | Souza et al. |
| 5,611,784 A | | 3/1997 | Barresi et al. |
| 5,697,899 A | | 12/1997 | Hillman et al. |
| 5,733,259 A | | 3/1998 | Valcke et al. |
| 5,800,397 A | | 9/1998 | Wilson et al. |
| 5,827,219 A | | 10/1998 | Uber, III et al. .............. 604/30 |
| 5,830,194 A | | 11/1998 | Anwar et al. |
| 5,842,468 A | | 12/1998 | Denyer et al. |
| D404,717 S | | 1/1999 | Duchon et al. |
| 5,865,805 A | | 2/1999 | Ziembra |
| 5,868,710 A | | 2/1999 | Battiato et al. |
| 5,879,627 A | | 3/1999 | Tanihata |
| 5,882,343 A | | 3/1999 | Wilson et al. |
| 5,885,216 A | | 3/1999 | Evans, III et al. .......... 600/431 |
| 5,913,844 A | | 6/1999 | Ziembra et al. |
| 5,916,165 A | | 6/1999 | Duchon et al. |
| 5,925,016 A | * | 7/1999 | Chornenky et al. ........... 604/19 |
| 5,976,112 A | | 11/1999 | Lyza, Jr. |
| 5,988,587 A | | 11/1999 | Duchon et al. |
| 5,993,779 A | * | 11/1999 | Mori .......................... 604/508 |
| 6,030,368 A | | 2/2000 | Anwar et al. |
| 6,063,052 A | | 5/2000 | Uber, III et al. |
| 6,099,502 A | | 8/2000 | Duchon et al. ............. 604/131 |
| 6,139,570 A | * | 10/2000 | Saadat et al. ................ 607/105 |
| 6,139,571 A | * | 10/2000 | Fuller et al. ................. 604/113 |
| 6,171,276 B1 | | 1/2001 | Lippe et al. |
| 6,221,045 B1 | | 4/2001 | Duchon et al. |
| 6,295,990 B1 | * | 10/2001 | Lewis et al. ................. 604/509 |
| 6,488,659 B1 | * | 12/2002 | Rosenman .................. 604/113 |

* cited by examiner

FLUID INJECTION APPARATUS WITH IMPROVED CONTRAST VISUALIZATION

FIELD OF THE INVENTION

The invention generally relates to fluid injection apparatus and, more particularly, relates to manually operated syringes.

BACKGROUND OF THE INVENTION

Many medical procedures require the injection of fluid. One example is angiography. Angiography is a procedure used in the detection and treatment of abnormalities or restrictions in blood vessels. During angiography, a radiographic image of a vascular structure is obtained by injecting radiopaque fluid or contrast through a catheter into a vein or artery. Vascular structure fluidically connected with the vein or artery in which the injection occurs is filled with the contrast material. X-rays are then passed through the region of the body in which the contrast material was injected, with the x-rays being absorbed by the contrast material, creating a radiographic outline or image of the blood vessel containing the contrast material. The x-ray image of the blood vessels filled with the contrast material is usually recorded onto film or videotape and then displayed on a fluoroscope monitor.

The speed with which the injection of contrast occurs enhances the resulting radiographic image because the speed of injection counteracts the flow of blood through the vessels that continually carries or flushes the contrast away. The faster the injection of contrast means a higher concentration of the contrast during the x-ray imaging and therefore a higher radiopacity of the blood vessels. Due to the high viscosity of the contrast material, and the flow resistance in the catheter and other fluid channels, the force required for rapid injection of a contrast is relatively high.

An additional factor contributing to the high forces required for plunger depression is that as current technology has evolved, the catheters used for angiography have reduced in size. The outlet diameters of the catheters have been reduced to four or five French size catheters. As a result, the force required to inject into the arteries has increased significantly.

Currently, manual syringes are used to inject contrast into most arteries. When large flow rates of contrast are required, as is the case for ventrilography (injecting into the left ventricle), a power injector is typically used because manual syringes cannot be operated with sufficiently high flow rate due to the inability to apply enough manual force on the syringe plunger. The power injector is operated by first setting a flow rate and an injection volume. The operator then activates the system by pressing a button on a hand controller which actuates a motor or the like for injecting the contrast. Examples of such power injectors are disclosed in U.S. Pat. Nos. 5,515,851 and 5,916,165.

However, while such power injectors are preferable in certain applications, in other instances, it would be advantageous to use a manual syringe. One advantage of using a manual syringe is that the operator is provided with more direct control of the injection. For example, if resistance is encountered during the injection process, the operator can detect the resistance due to an increase in the pressure, and thus the force required to manually depress the plunger.

It would therefore be advantageous to provide a fluid injection apparatus which enables the injection to be performed manually, but which reduces the force required for such manual operation without employing a power injector.

SUMMARY OF THE INVENTION

In accordance with one aspect of the invention, a fluid injection apparatus adapted to inject fluid is provided which comprises an input device, a catheter, and an improved visualization device. The catheter is in fluid communication with the input device. The improved visualization device is adapted to increase the speed with which fluid may be injected.

In accordance with another aspect of the invention, a method of manually injecting fluid is provided which comprises the steps of retracting a plunger from a syringe cylinder and drawing fluid into the cylinder, depressing the plunger into the cylinder forcing the fluid out an outlet of the cylinder, increasing the speed with which fluid may be injected, and injecting the fluid into a patient.

In accordance with another aspect of the invention, a manually operated fluid injection apparatus is provided which comprises a syringe, a manifold, a fluid line, a catheter, a source of fluid, and a heater. The syringe includes a movable plunger, while the manifold includes a plurality of inlet ports in first and second ends. The syringe is connected to the first end of the manifold. The catheter is connected to the second end of the manifold. The source of fluid is in communication with one of the manifold inlet ports via the fluid line, while the heater is operatively associated with one of the syringe, manifold, fluid line, catheter, or source of fluid.

In accordance with another aspect of the invention, a manually operated fluid injection apparatus is provided which comprises a syringe, a manifold, a fluid line, a catheter, a source of fluid, and an expandable ring. The syringe includes a movable plunger, while the manifold includes a plurality of inlet ports in first and second ends. The syringe is connected to the first end of the manifold. The catheter is connected to the second end of the manifold. The source of fluid is in communication with one of the manifold inlet ports via the fluid line, while the expandable ring is associated with the catheter and is expandable after catheter insertion and prior to injection to constrict blood flow.

In accordance with another aspect of the invention a manually operated fluid injection system is provided which comprises a manipulable input device, and a heater associated with the input device and adapted to increase the temperature of fluid prior to injection.

In accordance with another aspect of the invention a manually operated fluid injection system is provided which comprises a manipulable input device, a catheter connected to the input device, and an expandable member associated with the catheter and adapted to expand after the catheter is inserted into a patient to restrict blood flow during injection.

These and other aspects and features of the invention will become more apparent from the following detailed description when taken in conjunction with the accompanying drawings.

Figure 1:
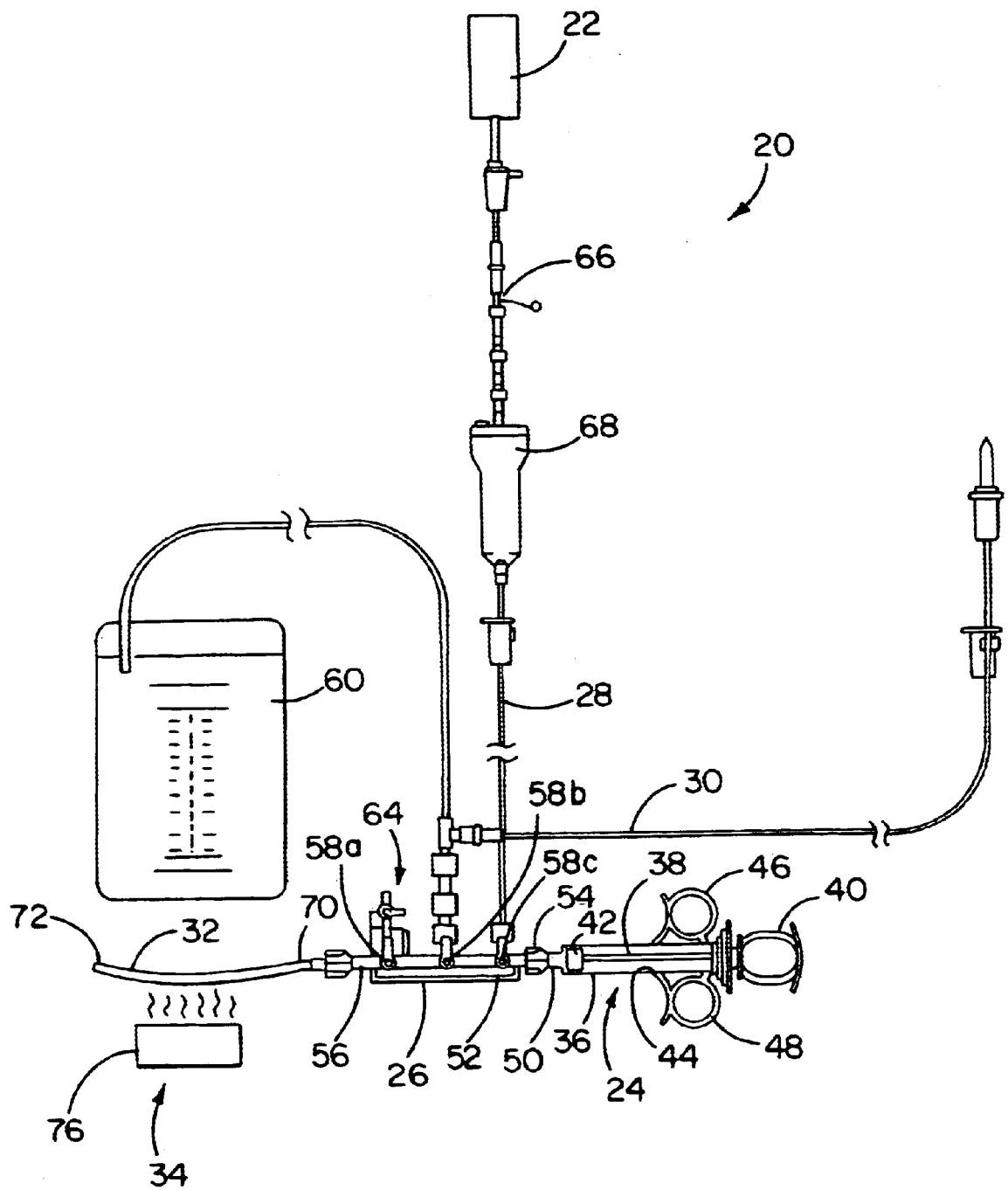
FIG. 1 is a schematic representation of a manual fluid injection apparatus constructed in accordance with the teachings of the invention.

While the invention is susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the invention as defined by the appended claims.

DETAILED DESCRIPTION OF THE PREFERRED EMBODIMENTS

Referring now to the drawings, and with specific reference to FIG. 1, a manually operated fluid injection apparatus constructed in accordance with the teachings of the invention is generally depicted by reference numeral 20. The apparatus 20 is depicted in reference to a manually operated apparatus 20 for the injection of radiopaque contrast from a supply 22 to a patient (not shown). However, it is to be understood that the teachings of the invention can be used for the injection of other fluids as well, and in power-assisted, or automatic injection systems as well.

As shown in FIG. 1, the apparatus 20 includes a manually operated syringe 24, a manifold 26, a first fluid line 28, a second fluid line 30, a catheter 32, and an improved visualization device 34.

The syringe 24 includes a cylinder 36 in which a plunger 38 is disposed for translational movement. The plunger 38 includes a thumb ring 40, as well as a rubber or otherwise elastomeric stopper 42 engaging an inner circumferential surface 44 of the cylinder 36. First and second finger rings 46 and 48 extend from the cylinder 36 to facilitate operation of the syringe 24 in conjunction with the thumb ring 40. The cylinder 36 includes a reduced diameter outlet 50 connected to a first end 52 of the manifold 26. A threaded or other suitable coupling 54 is provided for attachment therebetween.

The manifold 26 includes the first end 52, a second end 56, and a plurality of valved inlet ports 58a, b, and c. As shown in FIG. 1, inlet port 58c is connected to the first fluid line 28 for receipt of contrast from the supply 22. The second inlet port 58b, is connected to a source of saline 60 by way of the second fluid line 30. The third inlet port 58a, is shown connected to a pressure transducer 64. The second end 56 of the manifold 26 is connected to the catheter 32.

The first fluid line 28, connecting the source of contrast 22 to the manifold 26, may include a valve 66 as well as a vent 68. The valve 66, which may be provided in the form of a stop cock, is provided to control flow of contrast from the source of contrast 22 to the manifold 26. The vent 68, is provided to aerate any air or gas within the first fluid line 28.

Figure 2:
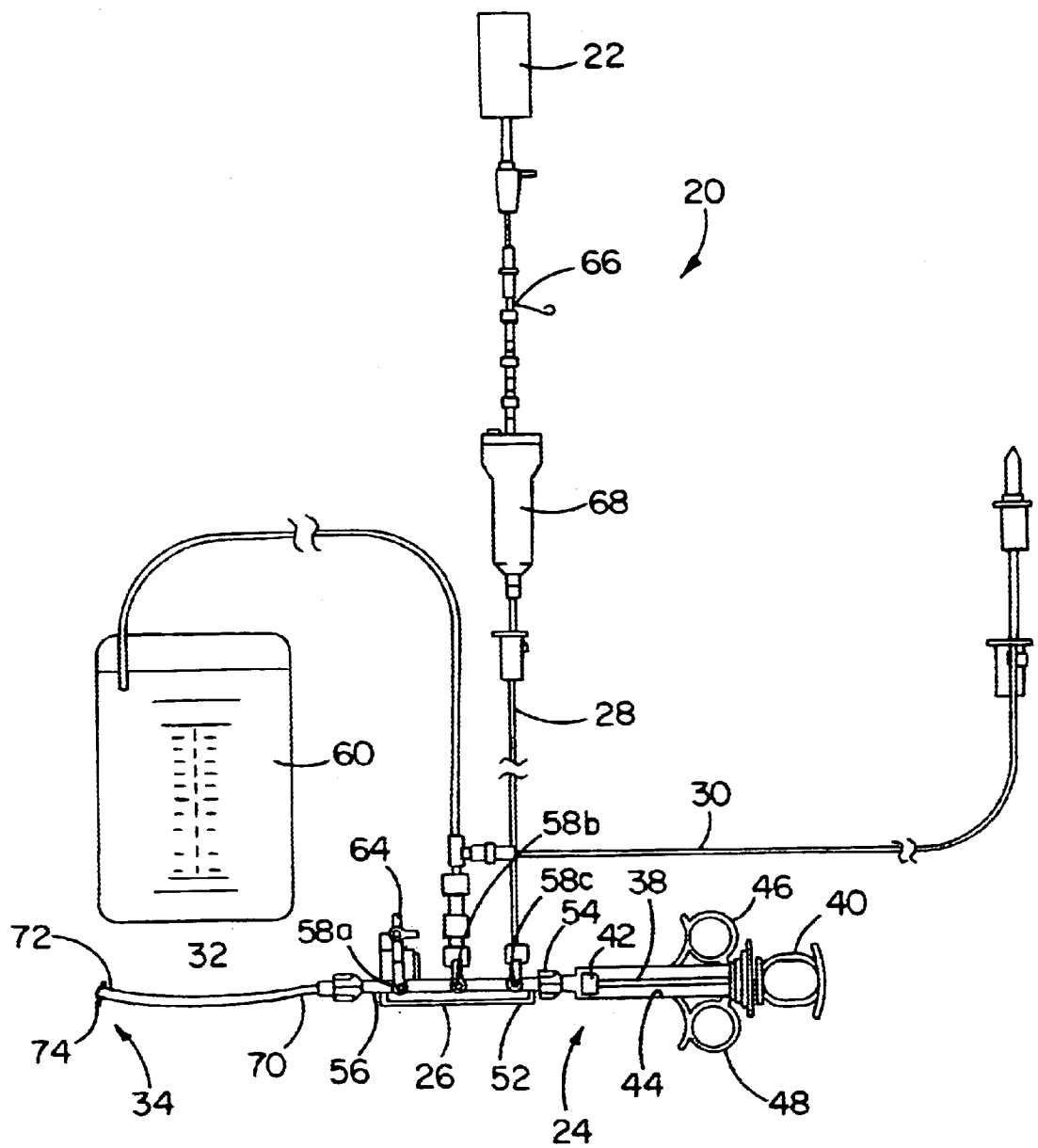
FIG. 2 is a block diagram of an alternative embodiment of a fluid injection apparatus constructed in accordance with the teachings of the invention.

The catheter 32 includes a proximal end 70, and a distal end 72. As shown in FIG. 2, in an alternative embodiment the distal end 72 of the catheter 32 may be provided with an expandable ring 74, the importance of which will be discussed in further detail herein. The expandable ring 74 may be provided in the form of an elastomeric hollow ring which upon introduction of compressed air or the like, may expand to increase the diameter of the catheter 32.

Referring again to FIG. 1, the improved visualization device 34 is shown proximate the catheter 32. The improved visualization device 34 may be provided in the form of a heater, or may include the expandable ring 74. The heater 76 can be provided in a variety of radiant, convective and conductive forms, including conventional heating coils which, upon electrical actuation, elevate temperature to thereby increase the temperature of the catheter 32 and thus the temperature of the contrast within the catheter 32. Alternatively, the heater 76 may be provided in the form of conduits or tubes wrapped around the catheter 32 or other parts of the apparatus 20 and through which a relatively warm fluid is passed for heating of the contrast. In a still further alternative, the heater 76 may be embedded directly in the apparatus 20. More specifically, resistor coils or other heating devices may be provided in the body of the syringe 24, the manifold 26, the first fluid line 28, the second fluid line 30, or the catheter 32. However, the inventor has found that it is beneficial to provide the heater 76 as close to the end of the catheter 32 inserted into the patient as possible to lessen the cooling effects of traveling through the apparatus 20.

The improved visualization devices 34 are provided to increase the speed with which the contrast may be injected to thereby minimize the effect of blood flow washing the contrast away and lessening the visual radiographic image generated. In the embodiment employing the heater 76, the speed is increased by elevating the temperature of the contrast, which in turn decreases its density and decreases its viscosity. Accordingly, the contrast is more easily injected. In the embodiment employing expandable ring 74, the size of the catheter 32 is increased after placement within the vascular structure of the patient. In so doing, blood flow is restricted through the vascular structure, momentarily, while the contrast is injected. The contrast therefore is injected with less mixing with blood flow and less dilution of the contrast. After injection of the contrast, the expandable ring can be deflated and the catheter 32 can be removed thereby allowing blood flow to return to normal. The heater 76 and the expandable ring 74 may be combined in the same system or apparatus 20.

Figure 3:
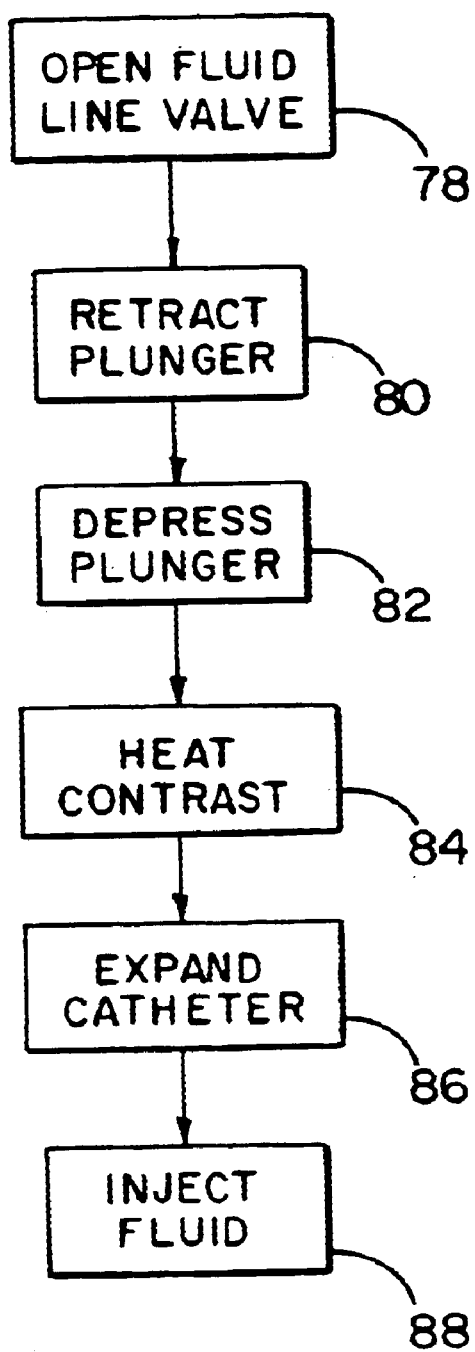
FIG. 3 is a flow chart of a sample sequence of steps which may be taken by a fluid injection system constructed in accordance with the teachings of the invention.

In operation, the apparatus 20 may be used to inject fluid into a patient with increased speed. As shown in FIG. 3, which is a sample depiction of steps which may be taken by the apparatus 20, after the valve 66 is opened, the process is initiated by opening the valved port 58c, as indicated by step 78. In so doing, fluid flow is communicated from the source of contrast 22, through the manifold 26 and to the outlet 50 of the syringe 24. The contrast 22 is able to enter the cylinder 36 of the syringe 24 upon retraction of the plunger 38, as indicated by step 80. More specifically, the retraction of the plunger 38 within the cylinder 36 creates a vacuum within the cylinder 36, thereby drawing the contrast into the syringe 24. The plunger 38 may be retracted a distance sufficient to fill the cylinder 36 to the appropriate volume. A series of indicia or graduations may be provided on the side of the cylinder to facilitate such operation.

Once the syringe 24 is filled to the appropriate volume, the plunger 38 is reciprocated back into the cylinder 36 as indicated by step 82. In so doing, the contrast 22 is forced from the cylinder 36 into the manifold 26, through the catheter 32, and into the patient. While passing through the components of the apparatus 20, the contrast fluid 22 is heated, as indicated by step 84. In so doing, the density and viscosity of the contrast 22 are decreased, and the force required by the user to depress the plunger 38 is decreased, and the speed of injection is increased.

In an optional step 86, the catheter 32 may be expanded in conjunction with the heating step 84. In so doing, the catheter 32 restricts blood flow through the vascular structure in which the catheter 32 is placed. The contrast 22 can therefore be injected into the patient in step 88 with lessened interference and dilution from blood flow. Once the contrast 22 is fully injected, the catheter can be deflated and removed. It is to understood that the expansion of the catheter step 86 may be conducted in the absence of the heating step 84, and similarly, that the heating of the contrast 84 can be conducted in the absence of the catheter expansion step 86.

From the foregoing, it can be seen by one of ordinary skill in the art that the teachings of the invention may be utilized to provide a manual fluid injection apparatus and method which reduces the force required by an operator to manually inject fluid into a patient, increases the speed of injection, and improves the contrast visualization on the resulting radiographic image.

What is claimed is:

1. An angiography device, comprising:
   a catheter inserted into a blood vessel;
   a source of radiopaque fluid;
   an injector fluidically connected to the source of radiopaque fluid and the catheter, the injector driving the radiopaque fluid from the source to the catheter and into the blood vessel;
   a heater heating the radiopaque fluid, the heater reducing the viscosity of the radiopaque fluid thus increasing the speed with which the radiopaque fluid is introduced into the blood vessel; and
   an expandable ring provided on the catheter, the expandable ring constricting blood flow through the blood vessel when expanded thus decreasing the speed with which the radiopaque fluid is diluted in the blood vessel.

2. The angiography device of claim 1, wherein the injector is a syringe.

3. The angiography device of claim 2, wherein the syringe is manually operated.

4. The angiography device of claim 1, further including a manifold having a plurality of ports, the injector, the source, and the catheter each being connected to one of the ports.

5. The angiography device of claim 1, wherein the heater is integrated into one of the injector, catheter, and source.

6. The angiography device of claim 1, wherein the heater employs a form of heating selected from the group of heating forms consisting of radiant, convective, and conductive heating.

7. An angiographic device, comprising:
   a catheter inserted into a blood vessel;
   a source of radiopaque fluid;
   an injector fluidically connected to the source of radiopaque fluid and the catheter and driving the radiopaque fluid from the source to the catheter and into the blood vessel; and
   an expandable ring provided on the catheter, the expandable ring constricting blood flow through the blood vessel when expanded thus decreasing the speed with which the radiopaque fluid is diluted in the blood vessel.

8. The angiographic device of claim 7, wherein the injector is a syringe.

9. The angiographic device of claim 8, wherein the syringe is manually operated.

10. The angiographic device of claim 7, further including a manifold having a plurality of ports, the injector, source, and catheter each being connected to one of the ports.

* * * * *